United States Patent [19]

Meilland

[11] Patent Number: Plant 6,163

[45] Date of Patent: May 3, 1988

[54] ROSE PLANT—MEIJUNKA VARIETY

[75] Inventor: Marie-Louise Meilland, Antibes, France

[73] Assignee: The Conard-Pyle Company, West Grove, Pa.

[21] Appl. No.: 833,612

[22] Filed: Feb. 27, 1986

[51] Int. Cl.[4] ..... A01H 5/00

[52] U.S. Cl. ..... Plt./11

[58] Field of Search ..... Plt. 11

*Primary Examiner*—Robert E. Bagwill

*Attorney, Agent, or Firm*—Burns, Doane, Swecker & Mathis

[57] ABSTRACT

A new and distinct variety of rose plant of the Intermediate Class is provided which forms elegant double blossoms. The blossoms are neyron pink in coloration and tend to be darker on the upper surface than on the under surface. The petals commonly exhibit attractive wavy edges. The plant exhibits a strong and vigorous growth habit and is well suited for greenhouse culture to produce cut flowers. Good resistance to fungus diseases is manifest.

1 Drawing Sheet

SUMMARY OF THE INVENTION

The new variety of Intermediate Class rose plant was created by artificial pollination wherein two parents were crossed which previously had been studied in the hope that they would contribute the desired characteristics. The female parent (i.e., the seed parent) of the new variety was an unintroduced seedling. The male parent (i.e., the pollen parent) of the new variety was the variety Samantha. The parentage of the new variety can be summarized as follows:

Unintroduced seedling × Samantha.

The seeds resulting from the above pollination were sown in a greenhouse and 55 plantlets were obtained which were physically and biologically different from each other. Selective study resulted in the identification of a single plant of the new variety.

It was found that the new variety of Intermediate Class rose plant of the present invention possesses the following combination of characteristics:

(a) forms elegant double neyron pink blossoms which tend to be darker on the upper surface than on the under surface, (b) forms petals which have wavy edges, (c) is particularly well suited for growing under greenhouse conditions, (d) exhibits a strong and vigorous growth habit, and (e) exhibits good resistance to fungal diseases.

The new variety well meets the needs of the cut flower industry since the plant is strong and vigorous and grows well under greenhouse conditions.

The new variety has been found to undergo asexual propagation by a number of routes, including budding, winter bench grafting, etc. The characteristics of the new variety has been found to be strictly transmissible by such asexual propagation from one generation to another.

The new variety has been named the Meijunka variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were observed during January while grafted on *Rosa indica* understock and growing in a greenhouse at Cap d'Antibes, France.

DETAILED DESCRIPTION

Figures 1, 2, 3, 4, 5, 6, 7, 8, 9, 10, 11, 12, 13, 14, 15, 16:
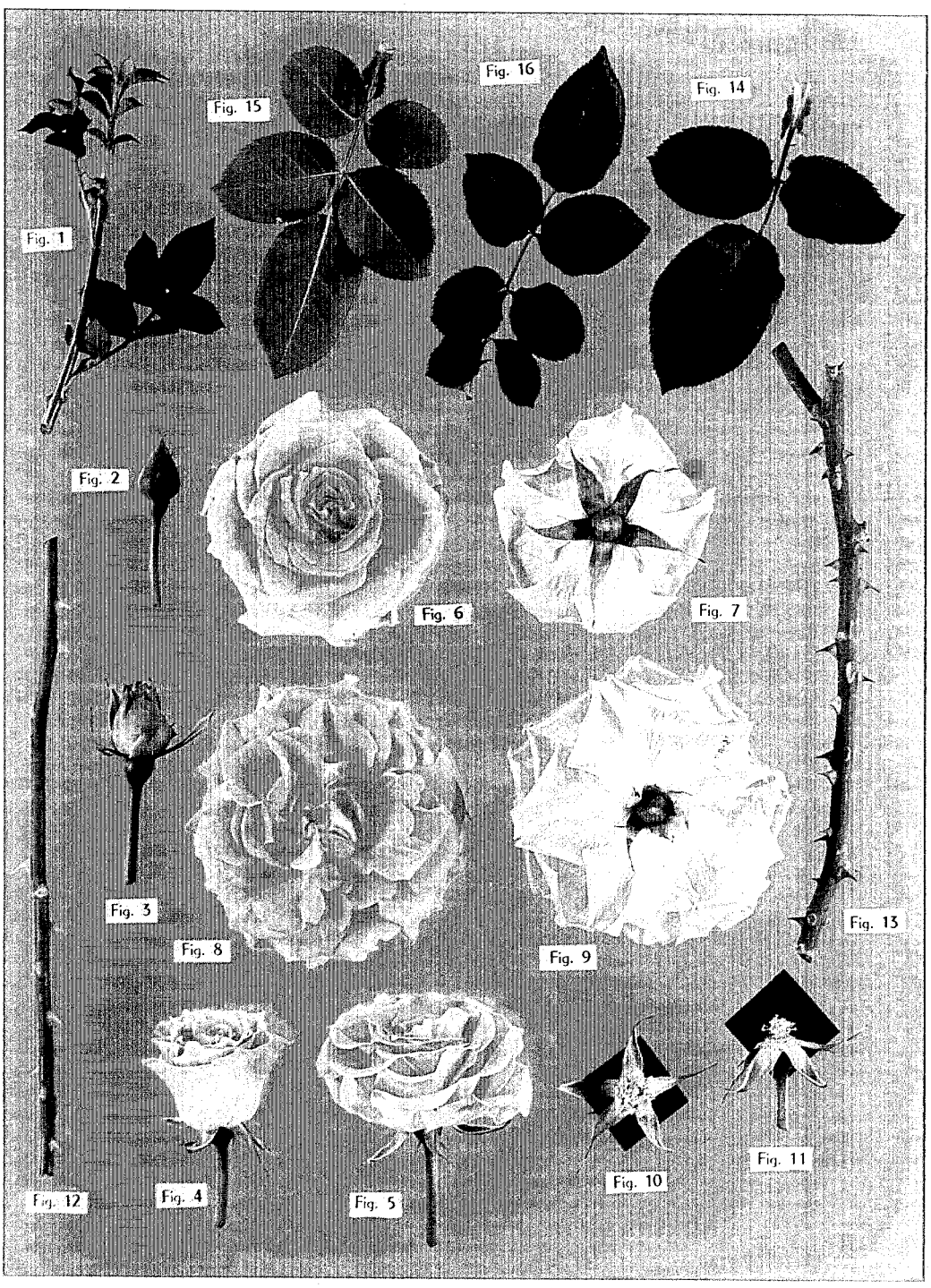
FIG. 1 illustrates a specimen of a young shoot.
FIG. 2 illustrates a specimen of a floral bud before the opening of the sepals.
FIG. 3 illustrates a specimen of a floral bud at the opening of the sepals.
FIG. 4 illustrates specimens of three floral buds at the opening of the petals.
FIG. 5 illustrates a specimen of a flower in the course of opening.
FIG. 6 illustrates a specimen of a fully open flower—plan view—obverse.
FIG. 7 illustrates a specimen of a fully open flower—plan view—reverse.
FIG. 8 illustrates a specimen of a fully open flower immediately prior to petal drop—plan view—obverse.
FIG. 9 illustrates a specimen of a fully open flower immediately prior to petal drop—plan view—reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates a specimen of a flowering stem.
FIG. 13 illustrates a specimen of a main branch.
FIG. 14 illustrates specimens of a leaf with three leaflets—upper surface.
FIG. 15 illustrates specimens of a leaf with five leaflets—under surface.
FIG. 16 illustrates a specimen of a leaf with seven leaflets—upper surface.

The chart used in the identification of the colors is that of The Royal Horticultural Society (R.H.S. Colour Chart). The description is based on observations made during January while grafted on *Rosa indica* understock and growing in a greenhouse at Cap d'Antibes, France.

Class: Intermediate.

Plant:

*Height.*—Plants which were pruned to a height of 85 cm. produced floral stems having a length of approximately 45 to 75 cm.

*Habit.*—Upright.

Branches:

*Color.*—Young stems: light green, Yellow-Green Group 146C, sometimes have reddish brown spots. Adult wood: dark green, Yellow-Green Group 146B.

Leaves:

*Petioles.*—Upper surface: noticeable venation, reddish brown on young foliage. Under surface: light green.

*Leaflets.*—Number: 3, 5, and 7 (most often). Shape: elliptic lancelate. Serration: simple and regular. General Appearance: very ample, and dense foliage which is somewhat glossy. Color (young foliage): upper surface: reddish brown. under surface: reddish brown. Color (adult foliage): upper surface: dark green, Yellow-Green Group 147A. under surface: medium green, Yellow-Green Group 147B.

Inflorescence:

*Number of flowers.*—Generally one per stem during greenhouse forcing, sometimes the buds at the top of the stem develop into flowering buds as well.

*Peduncle.*—Straight and rigid without thorns, its length is approximately 6 cm. on average.

*Buds.*—Shape: conical, opens like a cup. Length: approximately 3 cm. on average. Color upon opening: upper surface: neyron pink, Red Group 55A. under surface: neyron pink, Red Group 55B, changing to a lighter pink at the base of the bud (Red Group 55C).

*Flower.*—Diameter: approximately 12 cm. on average. Color (when opening begins): upper surface: neyron pink, Red Group 55A. under surface: neyron pink, Red Group 55B on margin of the petals, changing to 55C at the base of the petals. Color (when partially open): upper surface: neyron pink, Red Group 55A. under surface: pale neyron pink, Red Group 55C, on margin of the petals, lightening closer to the center. Color (at end of opening): upper surface: neyron pink, Red Group 55B. under surface: pale neyron pink, Red Group 55C, on margin of the petals, lightening closer to the center. Fragrance: none. Lasting quality: long. Petal number: approximately 35 on average. Petal form: round base, margins particularly on the outside of the blossoms are slightly curled and give a wavy overall appearance. Stamen number: approximately 141 on average. Anthers: straw colored with margins of light ochre.

Development:

*Disease resistance.*—Exhibits good resistance to major fungal diseases which commonly attack roses.

I claim:

1. A new and distinct variety of Intermediate Class rose plant characterized by the following combination of characteristics:

(a) forms elegant double neyron pink blossoms which tend to be darker on the upper surface than on the under surface, (b) forms petals which have wavy edges;

(c) is particularly well suited for growing under greenhouse conditions, (d) exhibits a strong and vigorous growth habit, and (e) exhibits good resistance to fungal diseases; substantially as herein shown and described.

* * * * *